(12) United States Patent
Nam et al.

(10) Patent No.: US 12,290,628 B2
(45) Date of Patent: May 6, 2025

(54) AGENT DELIVERY SYSTEMS AND METHODS OF USING THE SAME

(71) Applicant: Boston Scientific Scimed Inc., Maple Grove, MN (US)

(72) Inventors: Ra Nam, Lawrence, MA (US); Tony Soukalopoulos, Worcester, MA (US); Dennis Brian Hubbard, Jr., Lancaster, MA (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 537 days.

(21) Appl. No.: 17/210,166

(22) Filed: Mar. 23, 2021

(65) Prior Publication Data
US 2021/0299365 A1 Sep. 30, 2021

Related U.S. Application Data

(60) Provisional application No. 62/994,052, filed on Mar. 24, 2020.

(51) Int. Cl.
*A61M 11/00* (2006.01)
*A61M 5/31* (2006.01)
(Continued)

(52) U.S. Cl.
CPC ........ *A61M 11/003* (2014.02); *A61M 5/3145* (2013.01); *A61M 5/31511* (2013.01);
(Continued)

(58) Field of Classification Search
CPC ... A61B 17/00491; A61B 2017/00522; A61M 11/001; A61M 11/002; A61M 11/003
See application file for complete search history.

(56) References Cited

U.S. PATENT DOCUMENTS

| 471,854 A | 3/1892 | Howard |
| 881,238 A | 3/1908 | Hasbrouck |

(Continued)

FOREIGN PATENT DOCUMENTS

| CN | 101401956 B | 11/2012 |
| CN | 203971181 U | 12/2014 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — William R Carpenter
(74) *Attorney, Agent, or Firm* — Bookoff McAndrews, PLLC

(57) ABSTRACT

A medical device that includes a handle for conveying an agent having particles and a receiver having a first lumen defined by a first end and a second end. The receiver having an axis extending between the first end and the second end. The first end configured to receive the particles from the handle, and the second end in fluid communication with a second lumen having a cross-sectional dimension smaller than a cross-sectional dimension of the first lumen. Each of the cross-sectional dimensions of the first lumen and the second lumen is measured transverse to the axis. The second end is configured to receive the particles from the first end of the receiver. The second lumen is configured to control delivery of the agent to a delivery conduit in fluid communication with the second lumen based on sizes of the particles.

20 Claims, 5 Drawing Sheets

Figure 1:
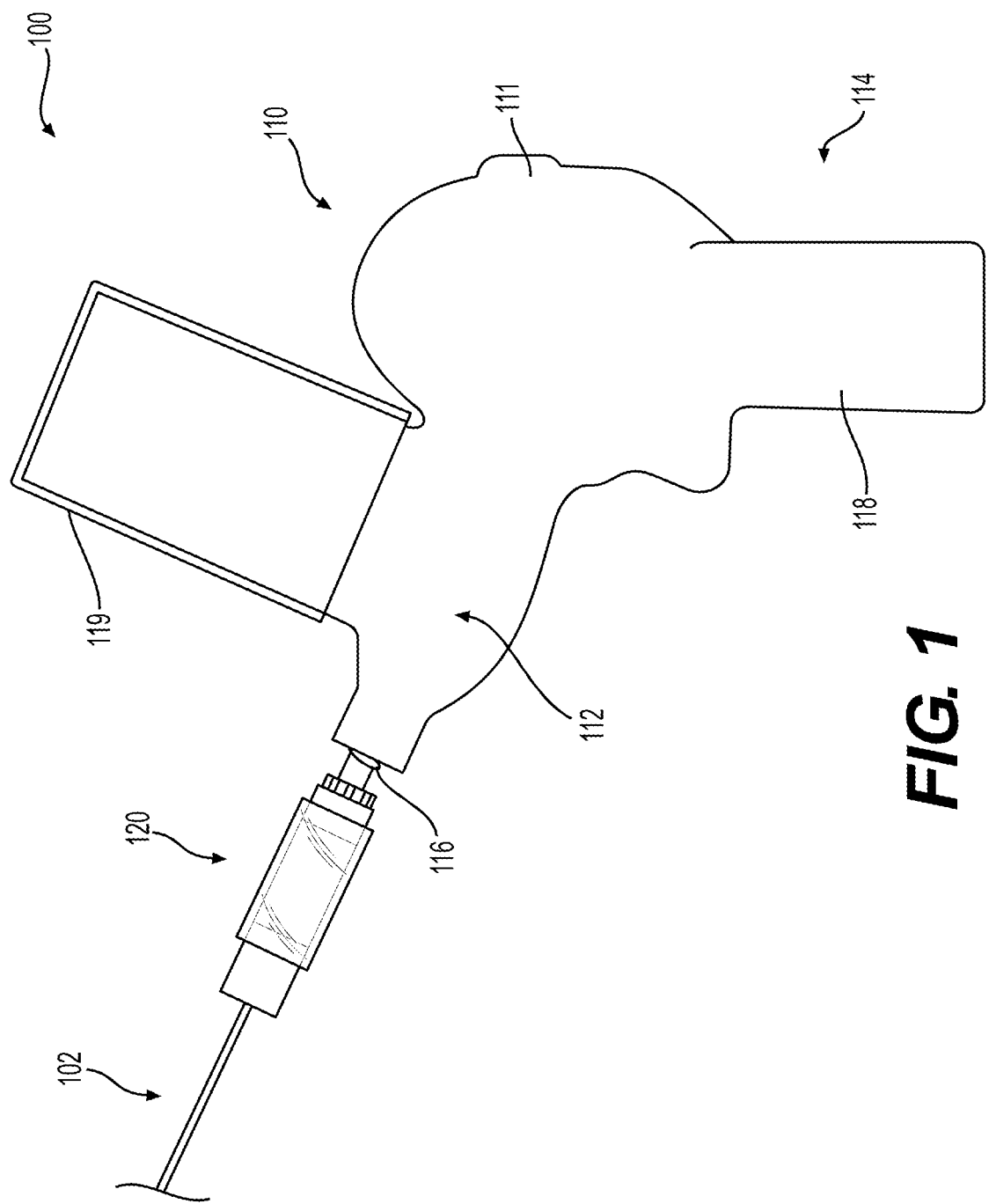

(51) Int. Cl.
  *A61M 5/315*  (2006.01)
  *A61M 25/00*  (2006.01)
(52) U.S. Cl.
  CPC ...... *A61M 5/31581* (2013.01); *A61M 11/007* (2014.02); *A61M 25/0023* (2013.01); *A61M 2202/064* (2013.01)

(56) References Cited

U.S. PATENT DOCUMENTS

| | | | |
|---|---|---|---|
| 1,145,520 | A | 7/1915 | Smith |
| 1,599,959 | A | 9/1926 | Buheiji |
| 1,732,566 | A | 10/1929 | McKendrick |
| 2,151,418 | A | 3/1939 | Bolte |
| 2,185,927 | A | 6/1940 | Shelanski |
| 2,478,715 | A | 8/1949 | Schmitt |
| 2,623,519 | A | 12/1952 | Cohen |
| 3,669,113 | A | 6/1972 | Altounyan et al. |
| 3,940,061 | A | 2/1976 | Gimple et al. |
| 4,184,258 | A | 6/1980 | Barrington et al. |
| 4,427,450 | A | 1/1984 | Kostansek |
| 4,457,329 | A | 7/1984 | Werley et al. |
| 4,620,847 | A * | 11/1986 | Shishov .................. A61M 5/00 604/58 |
| 4,806,167 | A | 2/1989 | Raythatha |
| 4,844,087 | A * | 7/1989 | Garg .................. A61B 10/0283 604/167.03 |
| 5,215,221 | A | 6/1993 | Dirksing |
| 5,231,983 | A | 8/1993 | Matson et al. |
| 5,273,531 | A | 12/1993 | Knoepfler |
| 5,281,197 | A | 1/1994 | Arias et al. |
| 5,312,331 | A | 5/1994 | Kneopfler |
| 5,312,333 | A | 5/1994 | Churinetz et al. |
| 5,366,122 | A | 11/1994 | Guentert et al. |
| 5,445,612 | A | 8/1995 | Terakura et al. |
| 5,470,311 | A | 11/1995 | Setterstrom et al. |
| 5,513,630 | A | 5/1996 | Century |
| 5,884,621 | A | 3/1999 | Matsugi et al. |
| 5,887,755 | A * | 3/1999 | Hood, III .................. B01F 25/25 222/394 |
| 5,951,531 | A | 9/1999 | Ferdman et al. |
| 6,003,512 | A | 12/1999 | Gerde |
| 6,484,750 | B1 | 11/2002 | Foos et al. |
| 6,554,022 | B2 | 4/2003 | Wakeman |
| 6,589,087 | B2 | 7/2003 | Mackal et al. |
| 6,598,087 | B1 | 7/2003 | Dixon, III et al. |
| 6,684,917 | B2 | 2/2004 | Zhu et al. |
| 6,708,712 | B2 | 3/2004 | Wakeman |
| 6,716,190 | B1 | 4/2004 | Glines et al. |
| 6,799,571 | B1 | 10/2004 | Hughes et al. |
| 7,178,547 | B2 | 2/2007 | Mackal |
| 7,311,270 | B2 | 12/2007 | Kapila |
| 7,334,598 | B1 | 2/2008 | Hollars |
| 7,361,300 | B2 | 4/2008 | Kelly et al. |
| 7,427,607 | B2 | 9/2008 | Suzuki |
| 7,455,248 | B2 | 11/2008 | Kablik et al. |
| 7,461,649 | B2 | 12/2008 | Gamard et al. |
| 7,544,177 | B2 | 6/2009 | Gertner |
| 7,563,299 | B2 | 7/2009 | Baptista da Costa et al. |
| 7,673,647 | B2 | 3/2010 | Mackal |
| 7,841,338 | B2 | 11/2010 | Dunne et al. |
| 7,892,205 | B2 | 2/2011 | Palasis et al. |
| 7,921,874 | B2 | 4/2011 | Tekulve et al. |
| 8,037,880 | B2 | 10/2011 | Zhu et al. |
| 8,097,071 | B2 * | 1/2012 | Burgess .................. B01D 39/2044 55/523 |
| 8,118,777 | B2 | 2/2012 | Ducharme et al. |
| 8,269,058 | B2 | 9/2012 | McCarthy et al. |
| 8,313,474 | B2 | 11/2012 | Campbell et al. |
| 8,360,276 | B2 | 1/2013 | Rogier et al. |
| 8,361,054 | B2 | 1/2013 | Ducharme et al. |
| 8,496,189 | B2 | 7/2013 | Lomond et al. |
| 8,673,065 | B2 | 3/2014 | Burgess et al. |
| 8,721,582 | B2 | 5/2014 | Ji |
| 8,728,032 | B2 | 5/2014 | Ducharme et al. |
| 8,741,335 | B2 | 6/2014 | McCarthy |
| 8,827,980 | B2 | 9/2014 | Ji |
| 8,910,627 | B2 | 12/2014 | Iwatschenko et al. |
| 8,951,565 | B2 | 2/2015 | McCarthy |
| 9,028,437 | B2 | 5/2015 | Ott et al. |
| 9,089,658 | B2 | 7/2015 | Dunne et al. |
| 9,101,744 | B2 | 8/2015 | Ducharme |
| 9,107,668 | B2 | 8/2015 | Melsheimer et al. |
| 9,132,206 | B2 | 9/2015 | McCarthy |
| 9,204,957 | B2 | 12/2015 | Gregory et al. |
| 9,205,170 | B2 | 12/2015 | Lucchesi et al. |
| 9,205,207 | B2 | 12/2015 | Ji |
| 9,205,240 | B2 | 12/2015 | Greenhalgh et al. |
| 9,308,584 | B2 | 4/2016 | Burgess et al. |
| 9,310,812 | B2 | 4/2016 | Costle et al. |
| 9,375,533 | B2 | 6/2016 | Ducharme et al. |
| 9,492,646 | B2 | 11/2016 | Hoogenakker et al. |
| 9,517,976 | B2 | 12/2016 | Mackal |
| 9,545,490 | B2 | 1/2017 | Iwatschenko et al. |
| 9,555,185 | B2 * | 1/2017 | Foster .................. A61M 5/3015 |
| 9,629,966 | B2 | 4/2017 | Ji |
| 9,636,470 | B2 | 5/2017 | Pohlmann et al. |
| 9,707,359 | B2 | 7/2017 | Kubo |
| 9,713,682 | B2 | 7/2017 | Eistetter et al. |
| 9,717,897 | B2 | 8/2017 | Rogier |
| 9,821,084 | B2 | 11/2017 | Diegelmann et al. |
| 9,839,772 | B2 | 12/2017 | Ducharme |
| 9,839,774 | B2 | 12/2017 | Bonaldo |
| 9,846,439 | B2 | 12/2017 | Carman et al. |
| 9,867,931 | B2 | 1/2018 | Gittard |
| 9,976,660 | B2 | 5/2018 | Stanton et al. |
| 10,004,690 | B2 | 6/2018 | Lee et al. |
| 10,010,705 | B2 | 7/2018 | Greenhalgh et al. |
| 10,017,231 | B2 | 7/2018 | Fawcett, Jr. |
| 10,036,617 | B2 | 7/2018 | Mackal |
| 10,065,004 | B2 | 9/2018 | Eder et al. |
| 10,173,019 | B2 | 1/2019 | Kaufmann et al. |
| 10,384,049 | B2 | 8/2019 | Stanton et al. |
| 10,463,810 | B2 * | 11/2019 | Groskopf .................. A61M 5/24 |
| 10,463,811 | B2 | 11/2019 | Lee et al. |
| 10,507,293 | B2 | 12/2019 | Goodman et al. |
| 10,646,706 | B2 | 5/2020 | Rogier |
| 10,730,595 | B2 | 8/2020 | Fawcett |
| 10,751,523 | B2 | 8/2020 | Rogier |
| 10,806,853 | B2 | 10/2020 | Gittard |
| 10,840,814 | B2 | 12/2020 | Fawcett |
| 10,850,814 | B2 | 12/2020 | Fawcett |
| 10,994,818 | B2 | 5/2021 | Hernandez |
| 2003/0015557 | A1 * | 1/2003 | D'Alessio .................. A61B 17/00491 222/570 |
| 2003/0181931 | A1 | 9/2003 | Dieck et al. |
| 2004/0107963 | A1 | 6/2004 | Finlay et al. |
| 2004/0249359 | A1 | 12/2004 | Palasis et al. |
| 2005/0121025 | A1 | 6/2005 | Gamard et al. |
| 2005/0147656 | A1 | 7/2005 | McCarthy et al. |
| 2005/0220721 | A1 | 10/2005 | Kablik et al. |
| 2006/0004314 | A1 | 1/2006 | McCarthy et al. |
| 2006/0213514 | A1 | 9/2006 | Price et al. |
| 2007/0056586 | A1 | 3/2007 | Price et al. |
| 2007/0066920 | A1 | 3/2007 | Hopman et al. |
| 2007/0066924 | A1 | 3/2007 | Hopman et al. |
| 2007/0082023 | A1 | 4/2007 | Hopman et al. |
| 2007/0125375 | A1 | 6/2007 | Finlay et al. |
| 2007/0151560 | A1 | 7/2007 | Price et al. |
| 2007/0083137 | A1 | 8/2007 | Hopman et al. |
| 2007/0199824 | A1 | 8/2007 | Hoerr et al. |
| 2008/0021374 | A1 | 1/2008 | Kawata |
| 2008/0287907 | A1 | 11/2008 | Gregory et al. |
| 2009/0101144 | A1 | 4/2009 | Gamard et al. |
| 2009/0155342 | A1 | 6/2009 | Diegemann et al. |
| 2009/0281486 | A1 | 11/2009 | Ducharme |
| 2010/0121261 | A1 | 5/2010 | Kablik et al. |
| 2010/0292656 | A1 | 11/2010 | Groskopf et al. |
| 2010/0305505 | A1 * | 12/2010 | Ducharme .................. A61M 11/02 604/118 |
| 2011/0073200 | A1 | 3/2011 | Overvaag et al. |
| 2011/0274726 | A1 | 11/2011 | Guo et al. |
| 2011/0275989 | A1 * | 11/2011 | Yedida .................. A61B 17/00491 604/82 |

(56) References Cited

U.S. PATENT DOCUMENTS

| | | | |
|---|---|---|---|
| 2011/0308516 A1 | 12/2011 | Price et al. | |
| 2012/0035335 A1* | 2/2012 | Ladet | B01J 19/0066 |
| | | | 525/445 |
| 2014/0271491 A1 | 9/2014 | Gittard et al. | |
| 2015/0094649 A1* | 4/2015 | Gittard | A61M 13/00 |
| | | | 428/402 |
| 2015/0125513 A1 | 5/2015 | McCarthy | |
| 2016/0375202 A1 | 12/2016 | Goodman et al. | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |
| 2018/0369513 A1* | 12/2018 | Hannon | A61M 15/0086 |
| 2019/0134366 A1 | 5/2019 | Erez et al. | |
| 2019/0217315 A1 | 7/2019 | Maguire et al. | |
| 2019/0232030 A1* | 8/2019 | Pic | A61M 11/02 |
| 2019/0351107 A1 | 11/2019 | Sawhney et al. | |
| 2021/0024187 A1 | 1/2021 | Fawcett et al. | |
| 2021/0069485 A1 | 3/2021 | Rogier | |
| 2021/0162122 A1* | 6/2021 | Pic | A61B 17/00491 |
| 2022/0015749 A1* | 1/2022 | Sanders | A61B 17/00491 |

FOREIGN PATENT DOCUMENTS

| | | | | |
|---|---|---|---|---|
| DE | 60215438 T2 | 8/2007 | | |
| EP | 1208863 A2 | 5/2002 | | |
| EP | 3052168 B1 | 11/2019 | | |
| JP | H07118305 A | 5/1995 | | |
| JP | 2002165884 A | 6/2002 | | |
| JP | 2015503999 A | 2/2015 | | |
| WO | WO-9930834 A1 * | 6/1999 | | A61M 11/001 |
| WO | 03013552 A1 | 2/2003 | | |
| WO | 2004066806 A2 | 8/2004 | | |
| WO | 2005062896 A2 | 7/2005 | | |
| WO | 2006071649 A2 | 7/2006 | | |
| WO | 2006088912 A2 | 8/2006 | | |
| WO | 2008033462 A2 | 3/2008 | | |
| WO | 2009061409 A1 | 5/2009 | | |
| WO | WO-2010122103 A1 * | 10/2010 | | A61M 11/02 |
| WO | 2015050814 A1 | 4/2015 | | |
| WO | 2015062420 A1 | 5/2015 | | |
| WO | 2018157772 A1 | 9/2018 | | |
| WO | WO-2018195086 A1 * | 10/2018 | | A61M 11/002 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, COOK, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, an Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion dated Jul. 9, 2021, in counterpart International Patent Application No. PCT/US2021/023737 (34 pages, in English).

* cited by examiner

AGENT DELIVERY SYSTEMS AND METHODS OF USING THE SAME

CROSS-REFERENCE TO RELATED APPLICATIONS

This application claims the benefit of priority from U.S. Provisional Application No. 62/994,052, filed on Mar. 24, 2020, which is incorporated by reference herein in its entirety.

TECHNICAL FIELD

Various aspects of this disclosure relate generally to agent delivery systems, devices, and related methods. In embodiments, the disclosure relates to systems, devices, and related methods for delivering a therapeutic agent to a target treatment site, among other aspects.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a shaft of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered. Agent delivery may be achieved by utilizing pressurized fluid systems, for example. Such systems, however, may provide difficulties in controlling a delivery rate of the agent or a particulate size of the agent delivered to a target treatment site. Accordingly, a desired rate or size of the agent delivered may not be achieved, which may result in the agent clogging portions of the delivery device, in inconsistent dosing of agent, and/or the agent not reaching the treatment site deep within the GI tract.

SUMMARY

Aspects of the disclosure relate to, among other things, systems, devices, and methods for delivery of a dose of an agent of various sizes, among other aspects. Each of the aspects disclosed herein may include one or more of the features described in connection with any of the other disclosed aspects.

According to an example, a medical device may include a handle for conveying an agent having particles and a receiver having a first lumen defined by a first end and a second end. The receiver having an axis extending between the first end and the second end. The first end configured to receive the particles from the handle, and the second end in fluid communication with a second lumen having a cross-sectional dimension smaller than a cross-sectional dimension of the first lumen. Each of the cross-sectional dimensions of the first lumen and the second lumen is measured transverse to the axis. The second end is configured to receive the particles from the first end of the receiver. The second lumen is configured to control delivery of the agent to a delivery conduit in fluid communication with the second lumen based on sizes of the particles.

Any of the medical devices described herein may include any of the following features. The handle includes an enclosure for storing the agent and a filter mechanism disposed within the enclosure, the filter mechanism is configured to inhibit at least a portion of the agent from being conveyed to the receiver based on a size of the particles. The first end includes a third lumen having a cross-sectional dimension, measured transverse to the axis, smaller than the cross-sectional lumen of the first lumen, and greater than the cross-sectional lumen of the second lumen. The first lumen is disposed between the second lumen and the third lumen such that the third lumen is in fluid communication with the second lumen via the first lumen. The second lumen is defined by and extends through the second end, and the third lumen is defined by and extends through the first end. The second end of the receiver includes an interface adjacent the first lumen and configured to control delivery of the agent from the first lumen to the second lumen based on the sizes of the particles. The interface of the second end is a planar surface extending transverse to the first lumen, and defining an opening disposed along the planar surface that is in fluid communication with the second lumen. The interface of the second end is a tapered surface defining an opening that is in fluid communication with the second lumen. A length along the axis of the first lumen is greater than a length along the axis of each of the second lumen and the third lumen. The receiver is configured to mix the agent in the first lumen and separate the particles based on the sizes of the particles. The second end of the receiver is configured to receive a particle of the particles in the second lumen when a size of the particle is equal to or less than a predefined size. The medical device further including a plunger at least partially disposed within the enclosure, wherein the plunger is configured to move relative to the enclosure to move the agent within the enclosure. The plunger is configured to deliver a pressurized medium into the enclosure to move the agent toward the second end of the receiver. The medical device further including a handle coupled to the plunger, wherein the handle is configured to control movement of the plunger relative to the enclosure to control delivery of the agent from the enclosure to the receiver.

According to another example, a medical device may include an enclosure for storing an agent having particles, a delivery conduit, and a receiver disposed between and in fluid communication with the enclosure and the delivery conduit. The receiver having a longitudinal axis. The receiver includes a first lumen having a first cross-sectional dimension and a second lumen having a second cross-sectional dimension that is smaller than the first cross-sectional dimension. Each of the cross-sectional dimensions of the first lumen and the second lumen is measured transverse to the longitudinal axis. The first lumen is configured to capture particles of the agent received from the enclosure that have a first size, and the second lumen is configured to deliver to the delivery conduit particles of the agent that have a second size. The second size is smaller than the first size.

Any of the medical devices described herein may include any of the following features. The second lumen is configured to inhibit delivery to the delivery conduit of particles of the agent that have the first size. The medical device further including a ratchet configured to control a dose of the agent delivered from the enclosure to the receiver in response to actuation of a handle. The medical device further including a plunger at least partially disposed within the enclosure, wherein the plunger is movable relative to the enclosure and the ratchet is configured to control a movement of the plunger within the enclosure. The plunger includes a nozzle tip that directs a pressurized medium toward the agent stored in the enclosure for delivering the particles to the receiver.

According to another example, a method of delivering an agent via a medical device that includes an enclosure, a receiver, and a delivery tube, may include delivering the agent stored within the enclosure to a first lumen of the receiver. The agent is delivered in response to actuation of a source of pressure that is in fluid communication with the enclosure. The method may include delivering particles of the agent having a size less than a predefined size, to a second lumen of the receiver; and delivering the particles of the agent having the size less than the predefined size, to the delivery tube from the second lumen.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 1 is a side view of an exemplary medical device, according to aspects of this disclosure;

FIG. 2 is a perspective view of an exemplary receiver of the medical device of FIG. 1 including a recessed interface, according to aspects of this disclosure;

FIG. 3 is a cross-sectional side view of the receiver of FIG. 2, according to aspects of this disclosure;

FIG. 4A is a perspective view of another exemplary receiver of the medical device of FIG. 1 including a protruding interface, according to aspects of this disclosure;

FIG. 4B is a perspective view of another exemplary receiver of the medical device of FIG. 1 including a planar interface, according to aspects of this disclosure;

FIG. 5 is a side view of another exemplary medical system including a receiver of FIGS. 2-4B, according to aspects of this disclosure;

FIG. 6A is a partial perspective view of an exemplary plunger device of the medical system of FIG. 5 including a rounded tip, according to aspects of this disclosure;

FIG. 6B is a partial perspective view of another exemplary plunger device of the medical system of FIG. 5 including a rounded nozzle, according to aspects of this disclosure; and FIG. 6C is a partial perspective view of an exemplary plunger device of the medical system of FIG. 5 including a flat nozzle, according to aspects of this disclosure.

DETAILED DESCRIPTION

This disclosure is drawn to systems, devices, and methods for endoscopic delivery of, for example, a hemostatic agent, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Embodiments of this disclosure may be used to deliver a material to a target treatment site experiencing bleeding to achieve hemostasis or delivery of a therapeutic agent. For example, a hemostatic agent in the form of a powder may be delivered to treat a gastrointestinal bleed by a medical device that includes a receiver having a first lumen configured to receive particles of the powder. In some embodiments, the first lumen is in fluid communication with a second lumen having a cross-sectional dimension that is smaller than a cross-sectional dimension of the first lumen. In some embodiments, the second lumen is configured to control delivery of the powder to a delivery conduit in fluid communication with the second lumen based on sizes of the particles. Embodiments of the disclosure are not limited to such devices and methods, and instead may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various embodiments described herein include single-use or disposable medical devices.

In one example, a medical system for delivering the hemostatic material/agent may include a receiver for receiving the agent, funneling the agent to a catheter or other tube, for delivery to a target treatment site within a subject. In embodiments, the receiver is capable of permitting delivery of a desired particulate size of the agent and inhibiting delivery of an undesired particulate size to the subject. The receiver may include a funnel having a configuration that is configured to facilitate passage of a portion of the agent in the desired particulate size while retaining a portion of the agent within the receiver that is in the undesired particulate size. The configuration of the funnel may include a planar surface, a concave surface, or a convex surface that faces a flow of agent. Reference will now be made in detail to examples of the disclosure described above and illustrated in the accompanying drawings. Wherever possible, the same reference numbers will be used throughout the drawings to refer to the same or like parts.

FIG. 1 shows a side view of an exemplary medical device 100 in accordance with an example of this disclosure. The medical device 100 may include an insertion portion 102, a proximal portion 110, and a receiver 120. In some embodiments, the insertion portion 102 of the medical device 100 may include a catheter, an endoscope, a tube, etc. for delivering a material to a target treatment site within a patient. The proximal portion 110 may have a body 111 defined by a distal end 112 and a proximal end 114, with the distal end 112 of the proximal portion 110 including a port 116 for coupling one or more components of the medical device 100 to the proximal portion 110, such as, for example, the receiver 120.

The proximal end 114 of the proximal portion 110 may include a handle 118 that is sized and shaped to be manually graspable by a user of the proximal portion 110, for example, during a procedure. It should be appreciated that a size, shape, profile and/or configuration of the insertion portion 102 and/or the proximal portion 110 shown and described herein is merely illustrative such that they may include various other suitable arrangements without departing from a scope of this disclosure.

Still referring to FIG. 1, the proximal portion 110 of the medical device 100 may further include an enclosure 119 that is sized and shaped to store one or more components of the proximal portion 110 therein. In the embodiment, the enclosure 119 is positioned adjacent to the distal end 112 of the body 111, however, it should be understood that the enclosure 119 may be located at various other positions along the body 111. Additionally and/or alternatively, in other embodiments, the enclosure 119, for example the one or more components stored within the enclosure 119, may be disposed within the body 111. By way of example, the enclosure 119 of the proximal portion 110 may include a reservoir (not shown) storing one or more materials, such as, for example, an agent. The agent may include a therapeutic substance that is operable to coagulate blood, such as, for example, a hemostatic powder. In other embodiments, the agent may include various other materials and/or substances suitable for delivery.

By way of further example, the body 111 of the proximal portion 110 may include a pressurized medium source (not shown) storing a pressurized medium, such as, for example, a pressurized fluid. The pressurized fluid may include compressed air/gas, such as, for example, carbon dioxide ($CO_2$). The pressurized medium source may include a pneumatic system, such as, for example, a pressurized cylinder. As described in greater detail herein, the pressurized medium source may be configured to supply the reservoir in the enclosure 119 with a pressurized medium for mixing the one or more materials stored therein (e.g., the agent) and/or distributing the material to one or more other components of the medical device 100. Examples of the one or more components included in the proximal portion 110 of the medical device 100 may be in accordance with at least some of the teachings of U.S. App. No. 62/957,519, entitled "Devices and Methods for Delivering Powdered Agents," filed on Jan. 6, 2020, the disclosure of which is incorporated by reference herein.

Still referring to FIG. 1, the receiver 120 may be positioned at the distal end 112 of the proximal portion 110 and coupled to the body 111 via the port 116. In this instance, the receiver 120 is in fluid communication with one or more components of the proximal portion 110, such as, for example, the reservoir in the enclosure 119 and/or the pressurized medium source. The insertion portion 102 may be coupled to the receiver 120 at an end opposite of the port 116, and may be in fluid communication with the one or more components of the proximal portion 110 via the receiver 120 positioned therebetween.

Figure 2:
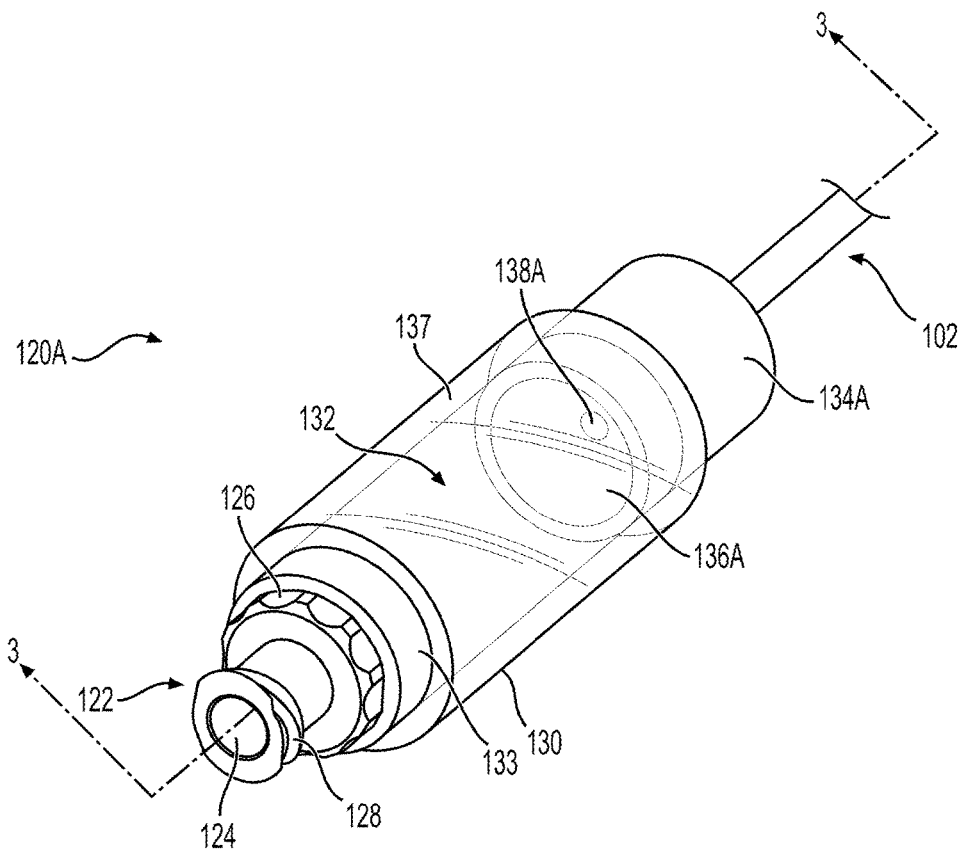

Referring now to FIG. 2, an exemplary schematic of a receiver 120A is shown. The receiver 120A may include a sheath 130 defined by a wall 137, a proximal end 133, and a distal end 134A. The wall 137 may be cylindrical or any other suitable shape. The sheath 130 defines a primary lumen 132 extending between the proximal end 133 and the distal end 134A. In the example, at least a portion of the proximal end 133 and the distal end 134A may be at least partially disposed within the primary lumen 132 of the sheath 130. The receiver 120A may further include an inlet head 122 at the proximal end 133 of the sheath 130, with the inlet head 122 defining an opening 124. In the example, the inlet head 122 extends proximally relative to the proximal end 133 of the receiver 120A such that the inlet head 122 is disposed external of the primary lumen 132 of the sheath 130.

The receiver 120A may further include a knob 126 at the proximal end 133. In the example, the knob 126 may be disposed between the inlet head 122 and the proximal end 133. In some examples, the knob 126 may be integral with the inlet head 122 such that the knob 126 and the inlet head 122 may form a unitary structure, while in other examples the knob 126 may be a separate component from the inlet head 122. The receiver 120A may further include one or more threads 128 disposed about an outer circumference of the inlet head 122. In this instance, the one or more threads 128 extend about the opening 124.

Still referring to FIG. 2, the knob 126 may include one or more graspable features thereon (e.g., recesses, protrusions, etc.) for manually manipulating the receiver 120A. With the knob 126 secured to the inlet head 122, the knob 126 may be configured to rotate the inlet head 122 in response to actuation (e.g., rotation) of the knob 126 relative to one or more other components of the medical device 110, such as, for example, the proximal portion 110. It should be understood that the knob 126 may be operable to couple (and decouple) the receiver 120A to the proximal portion 110 of the medical device 100 by rotatably engaging (and disengaging) the one or more threads 128 to corresponding threads of the body 111 (not shown) when the inlet head 122 is received within the port 116. In the example, the inlet head 122 of the receiver 120A may include a male luer connector for connection to a corresponding female luer connector positioned at the port 116 of the proximal portion 110. In this instance, with the inlet head 122 coupled to the port 116, the opening 124 may be fluidly coupled to the one or more components of the proximal portion 110, such as, for example, the reservoir, the pressurized medium source, and the like.

Figure 3:
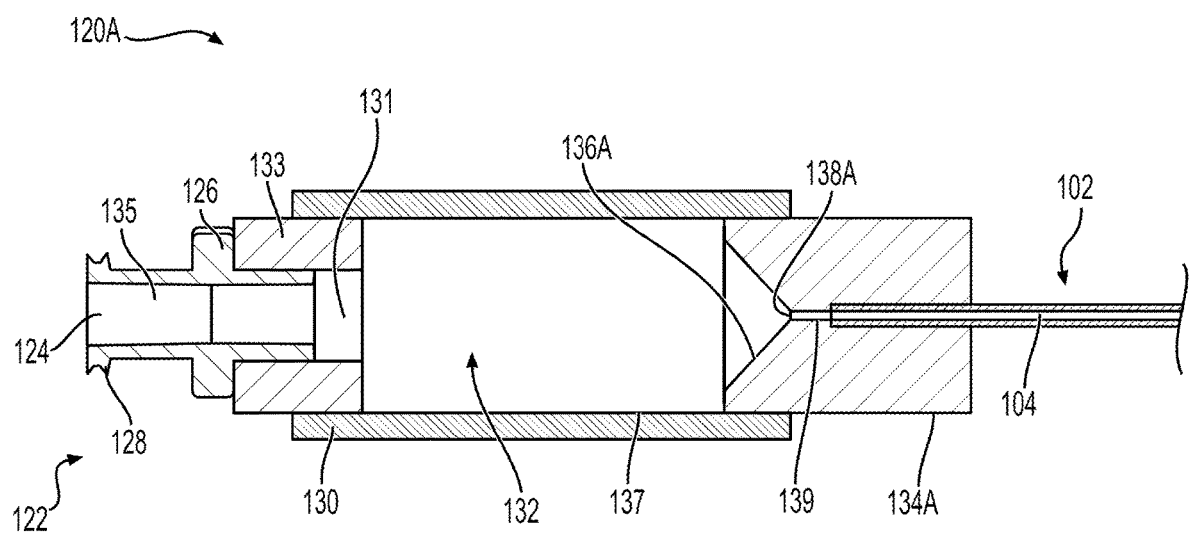

Referring now to FIG. 3, the receiver 120A may be coupled to the insertion portion 102 of the medical device 100 at the distal end 134A. The primary lumen 132 of the sheath 130 may be in fluid communication with a proximal lumen 131 of the proximal end 133, an inlet lumen 135 of the inlet head 122, and a distal lumen 139 of the distal end 134A. In this instance, the opening 124 of the inlet head 122 may be in fluid communication with the inlet lumen 135, with the inlet lumen 135 fluidly coupled to the primary lumen 132 of the sheath 130 via the proximal lumen 131 of the proximal end 133. A longitudinal length of the receiver 120A may define a longitudinal axis (not shown) extending between the proximal end 133 and the distal end 134A.

It should be appreciated that the proximal lumen 131 of the proximal end 133 may have a first cross-sectional dimension, the distal lumen 139 of the distal end 134A may have a second cross-sectional dimension, and the inlet lumen 135 of the inlet head 122 may have a third cross-sectional dimension. In the example, the cross-sectional dimensions of the proximal lumen 131, the distal lumen 139, and the inlet lumen 135 may be transverse relative to the longitudinal axis of the receiver 120A. In the example, a length along the longitudinal axis of the primary lumen 132 is greater than a length along the longitudinal axis of each of the proximal lumen 131, the distal lumen 139, and/or the inlet lumen 135.

In the example, the first cross-sectional dimension of the proximal lumen 131 may be different than the second cross-sectional dimension of the distal lumen 139 and/or the third cross-sectional dimension of the inlet lumen 135. For example, the first cross-sectional dimension of the proximal lumen 131 may be relatively greater than the second cross-sectional dimension of the distal lumen 139 and/or the third cross-sectional dimension of the inlet lumen 135. Further, in some examples, the third cross-sectional dimension of the inlet lumen 135 may be relatively greater than the second cross-sectional dimension of the distal lumen 139.

By way of further example, each of the first cross-sectional dimension of the proximal lumen 131, the second cross-sectional dimension of the distal lumen 139, and/or the third cross-sectional dimension of the inlet lumen 135 may be different than a cross-sectional dimension of the primary lumen 132 of the sheath 130, respectively. In the example, a cross-sectional dimension of the primary lumen 132 may be relatively greater than the first cross-sectional dimension of the proximal lumen 131, the second cross-sectional dimension of the distal lumen 139, and/or the third cross-sectional dimension of the inlet lumen 135, respectively. In some embodiments, the primary lumen 132 may include a diameter ranging from about 0.4 inches to about 0.6 inches, such as, for example, 0.5 inches. Further, the primary lumen 132 may include a longitudinal length ranging from about 0.9 inches to about 1.1 inches, such as, for example, 1.0 inches.

Still referring to FIG. 3, a lumen 104 of the insertion portion 102 may be in fluid communication with the primary lumen 132 of the sheath 130 via the distal lumen 139 of the distal end 134A when the insertion portion 102 is coupled to the receiver 120A at the distal end 134A. As described in further detail herein, the lumen 104 of the insertion portion 102 may include a cross-sectional dimension that is sized and shaped to receive particles of the agent stored in the reservoir of the enclosure 119 that have a predefined size. For example, in embodiments where the particles of the agent may be sized at approximately 325 to 425 micrometers, the lumen 104 of the insertion portion 102 may be sized with a diameter of about 0.05 inches. By way of further example, in embodiments where the particles of the agent may be sized at approximately 500 to 600 micrometers, the lumen 104 of the insertion portion 102 may be sized with a diameter of about 0.08 inches. In some examples, the second cross-sectional dimension of the distal lumen 139 may be at least equal to or less than a cross-sectional dimension of the lumen 104 of the insertion portion 102.

Referring to FIGS. 2-3, the distal end 134A of the receiver 120A may include an interface 136A and an opening 138A. In the example, the interface 136A defines a proximal surface of the distal end 134A that may be disposed within the primary lumen 132 of the sheath 130. The opening 138A may be positioned along the interface 136A of the distal end 134A and may be in fluid communication with the distal lumen 139 of the distal end 134A. In the example, the interface 136A, the opening 138A, and/or the distal lumen 139 of the distal end 134A may include a size, shape, and/or configuration that may be configured to inhibit delivery of one or more materials (or a subset thereof) from the sheath 130 to one or more components of the medical device 100, such as, for example, the insertion portion 102. Additionally and/or alternatively, the interface 136A, the opening 138A, and/or the distal lumen 139 may include a size, shape, and/or configuration that may be configured to permit delivery of one or more other materials (or a subset thereof) from the sheath 130 to one or more other components of the medical device 100, such as, for example, the insertion portion 102.

In the example, the interface 136A of the distal end 134A may have a recessed surface that extends distally away from the proximal end 133 of the receiver 120A. For example, the distal end 134A may have a concaved, recessed, sunken, funnel, and/or depressed configuration that defines the interface 136A. In this instance, with the opening 138A positioned at a center of the interface 136A, a cross-sectional dimension (e.g., diameter) of the interface 136A adjacent to the opening 138A may be less than a cross-sectional dimension (e.g., diameter) of the interface 136A relatively distal from the opening 138A. Accordingly, it should be appreciated that the interface 136A of the distal end 134A is relatively wider along a portion proximate to the proximal end 133 than an opposing portion proximate to the opening 138A and/or the insertion portion 102.

Still referring to FIGS. 2-3, the interface 136A of the distal end 134A may be configured to control a dose of a material (e.g., an agent) received in the sheath 130 and delivered to the insertion portion 102 via the distal lumen 139 of the distal end 134A. In this instance, the interface 136A may control a dose of the material delivered based on a size of the particles comprising the agent. A surface configuration of the interface 136A may guide and/or direct particles having a predefined size from the primary lumen 132 of the sheath 130 toward the opening 138A and into the lumen 104 of the insertion portion 102. Further, the surface configuration of the interface 136A may inhibit delivery of particles of the agent received in the sheath 130 and not having the predefined size from being received through the opening 138A and into the lumen 104.

The opening 138A and/or the distal lumen 139 of the distal end 134A may further be configured to control a dose of a material received in the sheath 130 and delivered to the insertion portion 102 based on a size of the particles of the agent. For example, a cross-sectional dimension of the opening 138A and/or of the distal lumen 139 may facilitate delivery of particles that have the predefined size from the primary lumen 132 to the lumen 104 of the insertion portion 102, while inhibiting delivery of those particles of the agent that do not have the predefined size. In the example, the predefined size of the particles may include a predetermined relationship between a cross-sectional dimension of the particle relative to a cross-sectional dimension of the lumen 104 of the insertion portion 102. For example, the predefined cross-sectional size of the particles may be equal to or less than approximately one-third, one-fourth, one-fifth, one-sixth, one-eight, one-ninth, one-tenth, or smaller than a cross-sectional dimension of the lumen 104 of the insertion portion 102. In other examples, the predefined size may include various other suitable cross-sectional dimensions relative to the insertion portion 102.

According to an exemplary method of using the medical device 100, a material may be initially stored in the reservoir of the enclosure 119 and the receiver 120A may be fluidly coupled to the body 111 of the proximal portion 110 via the port 116. In this instance, the inlet head 122 may be received in the port 116 and the one or more threads 128 may mesh with corresponding threads at the port 116. The threads 128 may be engaged to the body 111 of the proximal portion 110 in response to actuation (e.g., rotation) of the knob 126. Further, the insertion portion 102 may be fluidly coupled to the receiver 120A at the distal end 134A such that the lumen 104 of the insertion portion 102 may be in fluid communication with the reservoir of the enclosure 119 via the proximal lumen 131, the primary lumen 132, and the distal lumen 139.

In this instance, upon activation of the pressurized medium source of the proximal portion 110, a pressurized medium may be transmitted to the reservoir in the enclosure 119. The pressurized medium may cause the material stored in the reservoir to move therein, thereby producing a mixture of the material. In the example, the material may be an agent (e.g., hemostatic powder) comprising a plurality of particles having various sizes and/or shapes. It should be appreciated that each of the plurality of particles may have a different configuration relative to one another, including spherical, irregular, and/or asymmetrical profiles. Activation of the pressurized medium source of the medical device 100 may create a pressure change within the reservoir of the enclosure 119 that may move the agent from the reservoir and to the receiver 120A via the port 116.

In the example, the particles of the agent are delivered through the inlet head 122, into the proximal lumen 131 of the proximal end 133, and received within the primary lumen 132 of the sheath 130. With the plurality of particles of the agent received in the sheath 130, the receiver 120A may provide a further mixture of the agent in the primary lumen 132. Upon entering the sheath 130 of the receiver 120A via the proximal end 133, the plurality of particles of the agent may move within the primary lumen 132 and toward the distal end 134A. In this instance, the particles may encounter the interface 136A of the distal end 134A and, based on a size of the particles, be received through the opening 138A or deflected proximally (e.g., rearward) into the primary lumen 132 and back toward the proximal end 133. In other words, the receiver 120A of the medical device 100 may be configured to mix, separate, and/or sort the agent within the sheath 130 based on a cross-sectional dimension, size, and/or shape of the particles.

By way of example, the interface 136A of the distal end 134A may be configured to inhibit entry of one or more particles of the agent into the opening 138A and the distal lumen 139 when having a size greater than a predefined size. In the example, the predefined size of the particles may include a predetermined cross-sectional dimension that is equal to or less than approximately one-third, one-fourth, one-fifth, one-sixth, one-eight, one-ninth, one-tenth, or smaller than a cross-sectional dimension of the lumen 104 of the insertion portion 102. It should be appreciated that with the cross-sectional dimension of the opening 138A and/or the distal lumen 139 sized relatively smaller than the cross-sectional dimension of the proximal lumen 131, a subset of the particles received through the proximal end 133 and into the sheath 130 may be deliverable through the distal lumen 139. In this instance, a remainder of the particles not having the predefined size may be maintained in the primary lumen 132 of the sheath 130.

By facilitating delivery of the subset of particles of the agent having the predefined size through the opening 138A and the distal lumen 139, the receiver 120A may minimize clogging of the lumen 104 of the insertion portion 102 during a procedure. In this instance, the interface 136A, the opening 138A, and/or the distal lumen 139 of the distal end 134A may (e.g., individually and/or collectively) reduce delivery of oversized particles into the insertion portion 102, thereby decreasing incidents of the lumen 104 clogging and/or causing injury to a subject (e.g., patient). Accordingly, it should be appreciated that a predetermined subset of the material (e.g., particles of the agent having the predefined size) stored in the reservoir of the enclosure 119 may be delivered by the medical device 100 to a target treatment site within a subject due to the receiver 120A being fluidly coupled between the insertion portion 102 and the proximal portion 110.

With the cross-sectional dimension of the proximal lumen 131 sized relatively smaller than a cross-sectional dimension of the primary lumen 132, the particles of the agent received within the sheath 130 and not meeting the predefined size limitation may be maintained and/or suspended in the primary lumen 132 between the proximal end 133 and the distal end 134A. In other words, a subset of particles of the agent not having the predefined size and deflected toward the proximal end 133 from the distal end 134A are inhibited from being delivered through the proximal end 133 due to a flow of incoming fluid traveling through the inlet lumen 135 and toward the primary lumen 132.

In some examples, at least a portion of the particles not meeting the predefined size limitation may be deposited along a bottom surface (or other surface) of the sheath 130. In this instance, the particles deposited in the primary lumen 132 of the sheath 130 may form a stationary and/or static layer of material in the receiver 120A. It should be appreciated that a cross-sectional dimension of the proximal lumen 131 of the proximal end 133 may be sized greater than all, or substantially all, of the particles received within the primary lumen 132 of the sheath 130.

Figure 4A:
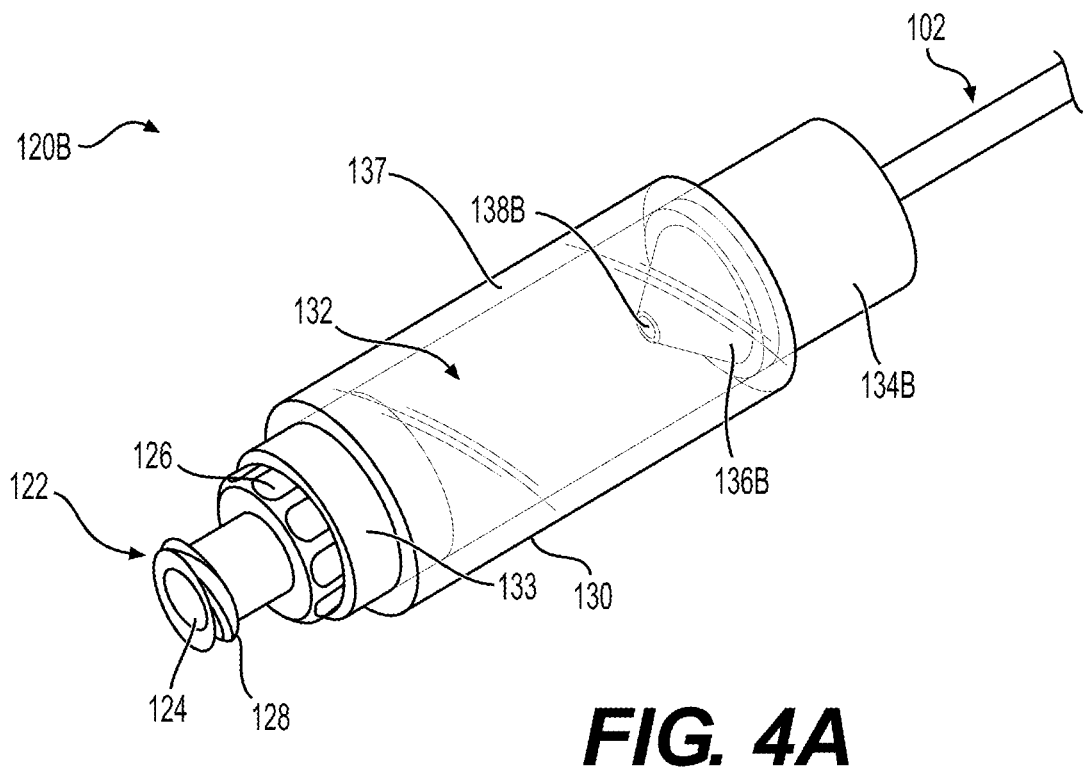

Referring now to FIG. 4A, another exemplary receiver 120B is depicted in accordance with an example of this disclosure. Except as otherwise described below, the receiver 120B may be substantially similar to the receiver 120A described above such that like reference numerals are used to identify like components. It should be understood that the receiver 120B may be configured and operable like the receiver 120A and that the receiver 120B may be readily incorporated into the medical device 100 described above.

For example, the receiver 120B may include a distal end 134B positioned along an end of the sheath 130 opposite of the proximal end 133. The distal end 134B may be at least partially disposed within the primary lumen 132 of the sheath 130 and may include an interface 136B and an opening 138B. The interface 136B defines a proximal surface of the distal end 1346 and the opening 1386 may be positioned along the interface 136B. The opening 138B may be in fluid communication with a distal lumen of the distal end 134B (similar to the distal lumen 139). In the example, the interface 136B, the opening 138B, and/or the distal lumen of the distal end 134B may include a size (e.g., cross-sectional size), shape, and/or configuration that may be configured to inhibit delivery of one or more materials (or a subset thereof) from the sheath 130 to the insertion portion 102. Additionally and/or alternatively, the interface 136B, the opening 138B, and/or the distal lumen of the distal end 134B may include a size (e.g., cross-sectional size), shape, and/or configuration that may be configured to permit delivery of one or more other materials (or a subset thereof) from the sheath 130 to the insertion portion 102.

In the example, the interface 136B of the distal end 134B may have a protruding surface that tapers proximally toward the proximal end 133 of the receiver 120B. In other words, the distal end 134B may have an extended, cone-shaped, and/or expanded configuration that defines the interface 136B. In some examples, the interface 136B may be configured to control a dose of a material (e.g., an agent) received in the sheath 130 and delivered to the insertion portion 102 via the distal lumen of the distal end 134B. In this instance, the interface 136B may control a dose of the material delivered based on a size of the particles comprising the agent. A configuration of the interface 136B may guide and/or direct particles having a predefined size from the primary lumen 132 of the sheath 130 toward the opening 138B and into the lumen 104 of the insertion portion 102. Further, the configuration of the interface 136B may inhibit delivery of particles of the agent received in the sheath 130 and not having the predefined size from being received within through opening 138B and into the lumen 104.

Figure 4B:
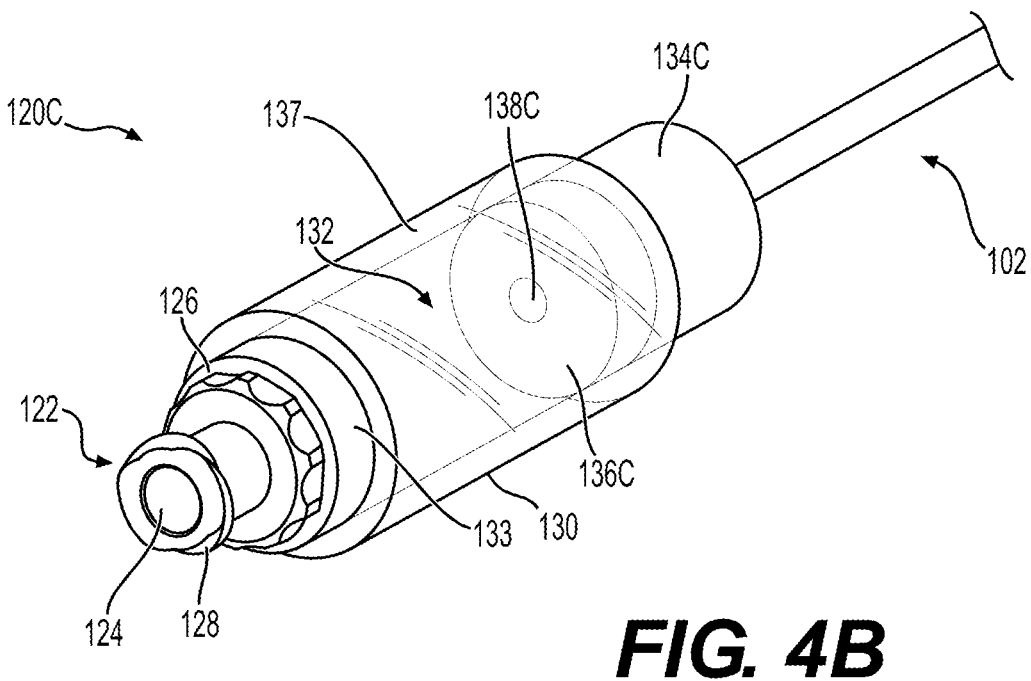

Referring now to FIG. 4B, another exemplary receiver 120C is depicted in accordance with an example of this disclosure. Except as otherwise described below, the receiver 120C may be substantially similar to the receiver 120A described above such that like reference numerals are used to identify like components. It should be understood that the receiver 120C may be configured and operable like the receiver 120A and that the receiver 120C may be readily incorporated into the medical device 100 described above.

For example, the receiver 120C may include a distal end 134C positioned along an end of the sheath 130 opposite of the proximal end 133. The distal end 134C may be at least partially disposed within the primary lumen 132 of the sheath 130 and may include an interface 136C and an opening 138C. The interface 136C defines a proximal surface of the distal end 134C and the opening 138C may be positioned along the interface 136C. The opening 138C may be in fluid communication with a distal lumen of the distal end 134C (similar to the distal lumen 139). In the example, the interface 136C, the opening 138C, and/or the distal lumen of the distal end 134C may include a size (e.g., cross-sectional size), shape, and/or configuration that may be configured to inhibit delivery of one or more materials (or a subset thereof) from the sheath 130 to the insertion portion 102. Additionally and/or alternatively, the interface 136C, the opening 138C, and/or the distal lumen of the distal end 134C may include a size (e.g., cross-sectional size), shape, and/or configuration that may be configured to permit delivery of one or more other materials (or a subset thereof) from the sheath 130 to the insertion portion 102.

In the example, the interface 136C of the distal end 134C may have a planar surface that extends transversely relative to a longitudinal axis of the receiver 120C. For example, the distal end 134C may have a flat and/or flush configuration that defines the interface 136C. In some examples, the interface 136C may be configured to control a dose of a material (e.g., an agent) received in the sheath 130 and delivered to the insertion portion 102 via the distal lumen of the distal end 134C. In this instance, the interface 136C may control a dose of the material delivered based on a size of the particles comprising the agent. A configuration of the interface 136C may guide and/or direct particles having a predefined size from the primary lumen 132 of the sheath 130 toward the opening 138C and into the lumen 104 of the insertion portion 102. Further, the configuration of the interface 136C may inhibit delivery of particles of the agent received in the sheath 130 and not having the predefined size from being received within through opening 138C and into the lumen 104.

Figure 5:
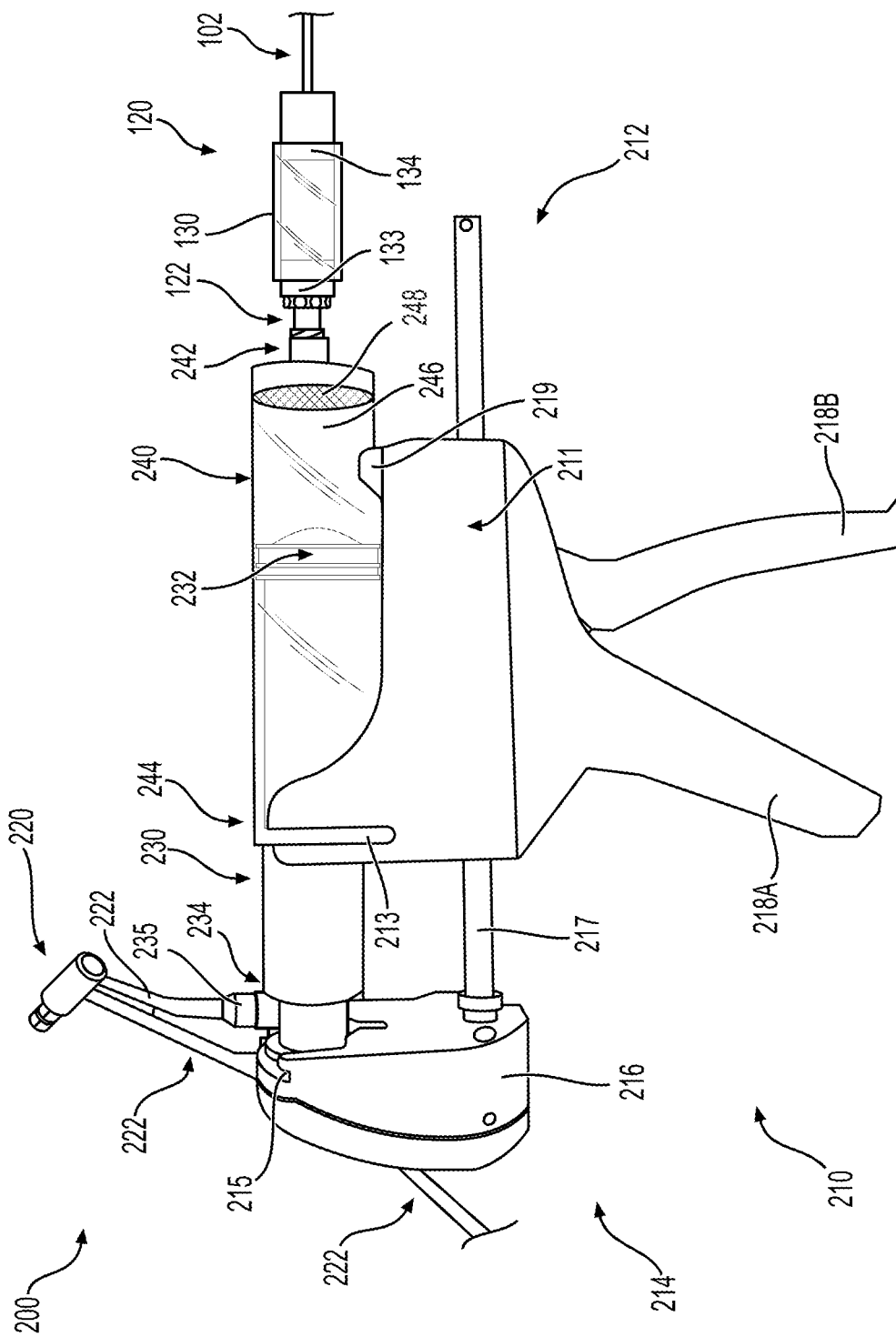

FIG. 5 shows a side view of an exemplary medical device 200 in accordance with an example of this disclosure. The medical device 200 may include an insertion portion 102, a proximal portion 210, and a receiver 120. It should be appreciated that the medical device 200 may include any of the exemplary receivers 120A, 120B, 120C and insertion portions 102 shown and described above without departing from a scope of this disclosure. The proximal portion 210 may have a first body 211 and a second body 216, with the first body 211 positioned at a distal end 212 of the proximal portion 210 and the second body 216 positioned at a proximal end 214 of the proximal portion 210. The first body 211 of the proximal portion 210 may be coupled to the second body 216 by a rod 217 extending therebetween. In the example, the rod 217 may be secured to the second body 216 and may extend through the first body 211. As described in further detail herein, the second body 216 and the rod 217 may be configured to move relative to the first body 211 in response to actuation of one or more other components of the medical device 200, such as, for example, one or more handles 218.

The proximal portion 210 of the medical device 200 may further include a switch 220, a plunger 230, and a syringe 240. The switch 220 of the proximal portion 210 may be fluidly coupled to a pressurized medium source (not shown) by one or more tubes 222 coupled to the switch 220 and the pressurized medium source, respectively. Further, the switch 220 of the proximal portion 210 may be fluidly coupled to the plunger 230 by one or more tubes 222 coupled thereto. As described further herein, the switch 220 is configured to selectively establish fluid communication between the pressurized medium source and the plunger 230 in response to actuation of the switch 220.

Still referring to FIG. 5, the plunger 230 of the proximal portion 210 may include a longitudinal length defined by, and extending between, a distal end 232 and a proximal end 234. It should be appreciated that the plunger 230 may define an inner lumen between the distal end 232 and the proximal end 234, and that is configured to supply a pressurized medium from the pressurized medium source. The proximal end 234 of the plunger 230 may include a port 235 that may be configured and operable to fluidly couple the plunger 230 to at least one of the one or more tubes 222. In this instance, the plunger 230 is in fluid communication with the switch 220 via the tube 222 received at the port 235. It should be understood that, in other examples, the port 235 may be positioned along various other portions of the plunger 230 than that shown and described herein without departing from a scope of this disclosure.

The proximal end 234 of the plunger 230 may be received within a slot 215 of the second body 216, thereby releasably securing the plunger 230 to the second body 216. As described in greater detail herein, with the proximal end 234 of the plunger 230 coupled to the second body 216 via the slot 215, the plunger 230 is configured to move relative to the first body 211 in response to movement of the second body 216 relative to the first body 211. The syringe 240 of the proximal portion 210 may include a longitudinal length defined by, and extending between, a distal port 242 and a proximal flange 244. The syringe 240 may define a lumen 246 between the distal port 242 and the proximal flange 244, that is configured to store a material therein, such as, for example, an agent (e.g., hemostatic powder) and receive the plunger 230.

In some embodiments, the syringe 240 may include one or more filter mechanisms 248 disposed within the lumen 246, such as, for example, at various suitable positions between the distal port 242 and the proximal flange 244. FIG. 5 shows one such filter mechanism 248. The filter mechanism 248 may include a mesh or a screen having a porous configuration. The pores of the filter mechanism 248 may be sized and/or shaped to at least partially inhibit a portion of the material (e.g., particulates of the hemostatic powder) from passing through the filter mechanism 248 (e.g., in a distal direction from a portion of the lumen 246 adjacent to proximal flange 244 to a portion of the lumen 246 adjacent to distal port 242) based on a particulate size of the material. Stated differently, the filter mechanism 248 may be configured to permit a portion of the material disposed within the lumen 246 to pass through the filter mechanism 248 (and toward the distal port 242) based on the particulate size of the material being smaller than a dimension of the pores (e.g., openings) on the filter mechanism 248. The filter mechanism 248 may reduce instances of the material clogging one or more components of the medical device 200 (e.g., the distal port 242, the receiver 120, the insertion portion 102) by maintaining the portion of material sized greater than the pores of the filter mechanism 248 within the lumen 246.

Still referring to FIG. 5, the proximal flange 244 of the syringe 240 may be configured and operable to releasably engage a slot 213 of the first body 211, thereby securing the syringe 240 to the first body 211 of the proximal portion 210. In some examples, the first body 211 may further include one or more retention mechanisms 219 along an exterior of the first body 211 for securing the syringe 240 thereon. It should be understood that, in other examples, the slot 213 and/or the one or more retention mechanism 219 may be positioned along various other portions of the first body 211 than that shown and described herein without departing from a scope of this disclosure. The distal end 232 of the plunger 230 may be disposed within the lumen 246 of the syringe 240 and movable relative to the distal port 242. The distal end 232 of the plunger 230 may provide a seal against the inner surface of the wall of the syringe 246.

As described in greater detail herein, the plunger 230 is configured to move relative to the syringe 240, and within the lumen 246, in response to movement of the second body 216 relative to the first body 211. In the example, the distal port 242 of the syringe 240 may be configured and operable to couple the syringe 240 to one or more components of the medical device 200, such as, for example, the receiver 120. In this instance, the inlet head 122 of the receiver 120 may be received in, and secured to, the distal port 242 of the syringe 240 thereby fluidly coupling the sheath 130 of the receiver 120 with the lumen 246 of the syringe 240.

The first body 211 of the proximal portion 210 may further include one or more handles 218A, 218B. The handle 218A may be movable and configured to pivot relative to a remainder of the first body 211, including the handle 218B. In the example, the handles 218A, 218B of the first body 211 may be coupled to a ratchet mechanism (not shown) of the proximal portion 210. For example, the ratchet mechanism may be disposed within the first body 211 and configured to control a rate of movement of the second body 216 relative to the first body 211. As handle 218A, 218B is pulled proximally, the ratchet mechanism is engaged to move the second body 216 relative to the first body 211.

Still referring to FIG. 5, with the plunger 230 secured to the second body 216 and the syringe 240 secured to the first body 211, the ratchet mechanism of the proximal portion 210 may further control a translation of the plunger 230 within the lumen 246 of the syringe 240 in response to actuation of the handles 218A, 218B. The ratchet mechanism may be operable to facilitate a progressive drive of the second body 216 and the plunger 230 along a plurality of incremental states relative to the first body 211 and the syringe 240, respectively, in response to mechanical actuation of the handles 218A, 218B. As described in greater detail herein, the ratchet mechanism of the proximal portion 210 may be configured to control a delivery flow rate of the material disposed within the lumen 246 of the syringe 240 by controlling an advancement of the plunger 230 relative to the syringe 240.

Figure 6A:
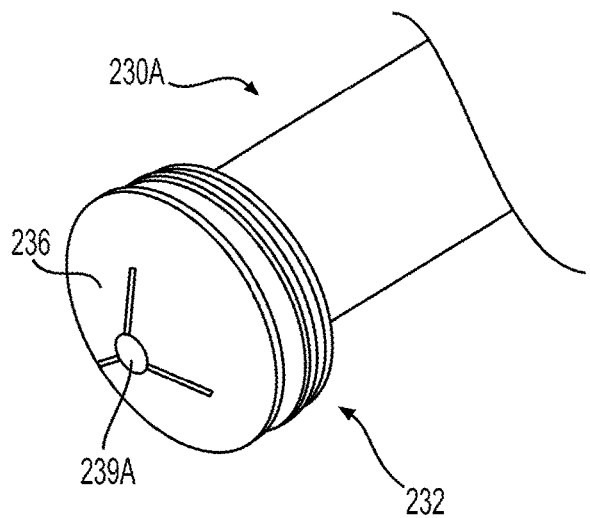
Figure 6B:
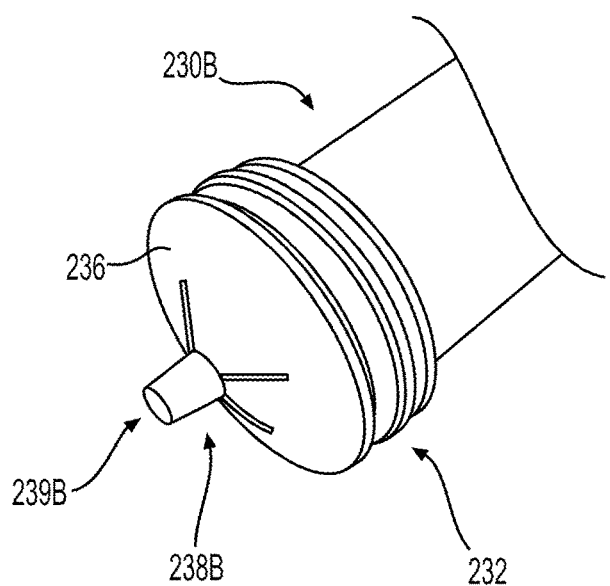
Figure 6C:
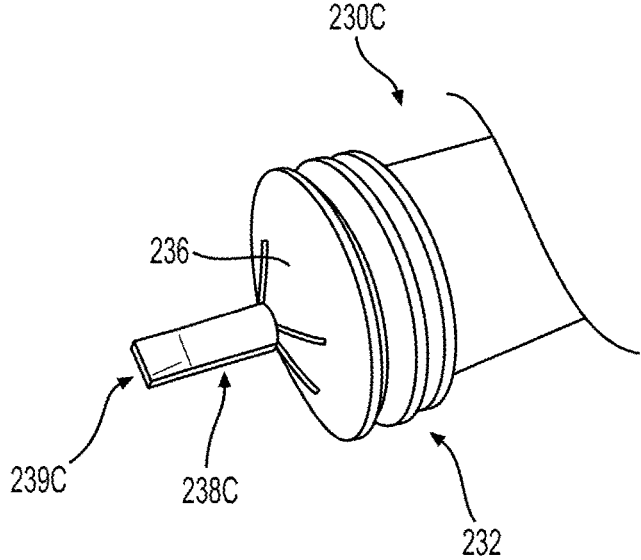

FIGS. 6A-6C illustrate partial perspective views of the distal end 234 of exemplary plungers 230A, 230B, 230C according to examples of this disclosure. Except as otherwise described below, the plungers 230A, 230B, 230C may be substantially similar to the plunger 230 described above such that like reference numerals are used to identify like components. It should be understood that the plungers 230A, 230B, 230C may be configured and operable like the plunger 230 and that the plungers 230A, 230B, 230C may be readily incorporated into the medical device 200 described above.

For example, referring initially to FIG. 6A, an exemplary plunger 230A may include a rounded head 236 at the distal end 232, with the rounded head 236 forming a nonplanar surface that may extend outwardly from the distal end 232. In some examples, the rounded head 236 includes a spherical, bulbous, and/or curved configuration that forms a transverse profile relative to a longitudinal axis of the plunger 230A. As described in greater detail herein, the rounded head 236 of the plunger 230A may be configured to direct and/or guide one or more materials disposed within the lumen 246 of the syringe 240 toward the distal port 242 as the plunger 230A is advanced therethrough.

The distal head 232 of the plunger 230A may further include an opening 239A positioned on the rounded head 236. In the example, the opening 239A is positioned along a center portion of the rounded head 236 and may be in fluid communication with an inner lumen of the plunger 230A. It should be understood that, in other examples, the opening 239A may be positioned along various other portions of the rounded head 236. The opening 239A on the rounded head 236 may be sized, shaped, and configured to deliver a material disposed within the inner lumen of the plunger 230A (e.g., a pressurized medium) outwardly from the distal end 232, such as, for example, into the lumen 246 of the syringe 240 when the plunger 230A is received therein.

Referring now to FIG. 6B, an exemplary plunger 230B may include a rounded nozzle 238B extending outwardly from the rounded head 236 of the distal end 232. In this instance, the rounded nozzle 238B includes a longitudinal length that extends distally relative to the rounded head 236 and is aligned parallel to a longitudinal axis of the plunger 230B. The distal head 232 of the plunger 230B may further include an opening 239B defined by the distal end of the rounded nozzle 238B. In the example, the opening 239B is positioned at a terminal end of the rounded nozzle 238B and may be in fluid communication with an inner lumen of the plunger 230B. It should be understood that, in other examples, the opening 239B may be positioned along various other portions of the rounded nozzle 238B and/or the rounded head 236.

The opening 239B on the rounded nozzle 238B may be sized, shaped, and configured to deliver a material disposed within the inner lumen of the plunger 230B outwardly from the distal end 232, such as, for example, into the lumen 246 of the syringe 240 when the plunger 230B is received therein. The rounded nozzle 238B may be sized, shaped, and configured to control a flow rate of the material delivered from the opening 239B and into the lumen 246 of the syringe 240. Further, a configuration of the rounded nozzle 238B may be operable to facilitate directing and/or guiding the material stored in the lumen 246 of the syringe 240 towards the distal port 232 while minimizing a compression of the material in the lumen 246 by the rounded head 236.

Still referring to FIG. 6B, with the rounded nozzle 238B having a relatively extended profile relative to the distal end 232 of the plunger 230B, the plunger 230B may allow for delivery of a pressurized medium to the agent in the syringe 240 while reducing an extent of movement (e.g., translation) of the distal end 232 within the lumen 246 and toward the distal port 232. Accordingly, it should be appreciated that the rounded nozzle 238B may be configured to decrease a compression of the material within the lumen 246 and a clogging of the distal port 242 in response to the rounded head 236 compacting the material by movement of the plunger 230B relative to the syringe 240.

Referring now to FIG. 6C, an exemplary plunger 230C may include a flat nozzle 238C extending outwardly from the rounded head 236 of the distal end 232. In this instance, the flat nozzle 238C includes a longitudinal length that extends distally relative to the rounded head 236 and is aligned parallel to a longitudinal axis of the plunger 230C. The distal head 232 of the plunger 230C may further include an opening 239C defined by the distal end of the flat nozzle 238C. In the example, the opening 239C is positioned at a terminal end of the flat nozzle 238C and may be in fluid communication with an inner lumen of the plunger 230C. It should be understood that, in other examples, the opening 239C may be positioned along various other portions of the flat nozzle 238C and/or the rounded head 236.

The opening 239C on the flat nozzle 238C may be sized, shaped, and configured to deliver a material disposed within the inner lumen of the plunger 230C outwardly from the distal end 232. The flat nozzle 238C may be sized, shaped, and configured to control a flow rate of the material delivered from the opening 239C. Further, an extended profile and/or configuration of the flat nozzle 238C may be operable to facilitate directing and/or guiding the material stored in the syringe 240 towards the distal port 232 while minimizing a compression of the material in the lumen 246 by the rounded head 236. Accordingly, it should be appreciated that the flat nozzle 238C may be configured to decrease a compression of the material within the lumen 246 and a clogging of the distal port 242 in response to the rounded head 236 compacting the material by movement of the plunger 230C relative to the syringe 240.

According to an exemplary method of using the medical device 200, a material may be initially stored in the lumen 246 of the syringe 240 and at least the distal end 232 of the plunger 230 may be disposed within the lumen 246. It should be appreciated that the medical device 200 may include any of the exemplary plungers 230A, 230B, 230C shown and described above without departing from a scope of this disclosure. The syringe 240 may be secured to the first body 211 by positioning the proximal flange 244 in the slot 213 and engaging the syringe 240 with the one or more retention mechanisms 219. With the second body 216 moved to a proximal-most (e.g., leftward) extent relative to the first body 211, the plunger 230 may be secured to the second body 216 by positioning the proximal end 234 in the slot 215. The switch 220 of the proximal portion 210 may be fluidly coupled to the port 235 of the plunger 230 via the tube 222.

The switch 220 may be further coupled to a pressurized medium source (not shown) via another tube 222, such that an inner lumen of the plunger 230 is in fluid communication with the pressurized medium source via the switch 220. The receiver 120 may be fluidly coupled to the syringe 240 via the distal port 242 by inserting the inlet head 122 in the distal port 242 and rotatably engaging the threads 128 with corresponding threads at the distal port 242 by actuating the knob 126. Further, the insertion portion 102 may be fluidly coupled to the receiver 120 at the distal end 134 such that the lumen 104 of the insertion portion 102 may be in fluid communication with the lumen 246 of the syringe 240 via the receiver 120.

In this instance, upon actuation of the switch 220, a pressurized medium from the pressurized medium source may be transmitted to the plunger 230 and outwardly from the distal end 232. The pressurized medium may cause the material stored in the lumen 246 to move therein, thereby producing a mixture of the material. In the example, the material may be an agent (e.g., hemostatic powder) comprising a plurality of particles having various sizes and/or shapes. Activation of the switch 220 of the medical device 200 may create a pressure change within the lumen 246 of the syringe 240 that may move the agent from the lumen 246 and to the receiver 120 via the distal port 242.

In the example, the particles of the agent are delivered through the inlet head 122 and received within the sheath 130 of the receiver 120. With the plurality of particles of the agent received in the sheath 130, the receiver 120 may provide a further mixture of the agent therein. The plurality of particles of the agent may move within the sheath 130 and be delivered through the distal end 134 to the insertion portion 102 in accordance with the method described in detail above. Accordingly, it should be appreciated that the receiver 120 may be configured to inhibit entry of one or more particles of the agent into the insertion portion 102 when having a size greater than a predefined size. In this instance, a remainder of the particles not having the predefined size may be maintained in the sheath 130 of the receiver 120.

Actuation of the handles 218A, 218B may provide a controlled advancement of the plunger 230 relative to the syringe 240, such as the distal end 232 toward the distal port 242. In this instance, movement of the distal end 232 relative to the lumen 246 may drive the agent stored in the syringe 240 toward the distal port 242 in response to the rounded head 236 abutting against and urging the agent distally. It should be appreciated that the rounded head 236 of the distal end 232 may be configured to unsettle the accumulated material deposited within the lumen 246 of the syringe 240 to facilitate delivery of the particles through the distal port 242.

A controlled movement of the plunger 230 relative to the syringe 240, provided by the ratcheting mechanism of the proximal portion 210, may allow the rounded head 236 to agitate the agent within the syringe 240 by disrupting a position and/or state of the particles stored along a bottom surface (or other surface) of the lumen 246. It should be appreciated that a movability of the particles of the agent may be improved for delivery by the pressurized medium through the distal port 242 in response to the rounded head 236 of the plunger 230 moving the particles.

In some examples, movement of the plunger 230 toward the distal port 242 may cause the agent (deposited along a bottom surface of the lumen 246) to accumulate relatively upward as a space within the syringe 240 between the distal end 232 and the distal port 242 decreases. In this instance, a top surface of the accumulated agent may rise (e.g., increase) as the space between the distal end 232 and the distal port 242 narrows, thereby aligning a level (e.g., height) of the top surface of the agent with the opening 239A, 239B, 239C of the plunger 230. Accordingly, movement of the plunger 230 relative to the syringe 240 may facilitate directing the pressurized medium from the opening 239A, 239B, 239C to the agent for delivery into the receiver 120 by positioning the particles of the agent in a flow path of the opening 239A, 239B, 239C.

With the switch 220 actuated to permit delivery of the pressurized medium into the plunger 230, the opening 239A, 239B, 239C at the distal end 232 may deliver the pressurized medium therethrough to direct the particles of the agent to the distal port 242. Additionally, in examples of the plunger 230B, 230C including the nozzle 238B, 238C, respectively, less movement of the plunger 230B, 230C may be required as the extension of the nozzle 238B, 238C may facilitate delivery of the pressurized medium to the agent while minimizing instances of the abutting head 236 compacting the agent within the lumen 246.

It should be appreciated that, in some examples, at least a portion of the agent stored in the syringe 240 may remain in the lumen 246 and not be received in the receiver 120, to minimize instances of clogging the insertion portion 102. Additionally, the portion of the agent received within the receiver 120 may be deposited along a bottom surface of the sheath 130 such that the agent forms a top surface therein. In this instance, the pressurized medium delivered into the receiver 120 from the plunger 230 may agitate the particles positioned along the top surface of the agent for delivery into the insertion portion 102.

Each of the aforementioned devices, assemblies, and methods may be used to provide controlled delivery of, for example, a hemostatic agent to a target treatment site. Any of the medical devices 100, 200, for example, the receivers 120A, 120B, 120C of the medical devices 100, 200 shown and described above, may be inserted into an endoscope, or like device, with imaging systems, lighting systems, etc., to assist in positioning the medical devices 100, 200. By providing a device that allows a user to treat a subject's tissue experiencing a bleed using a receiver 120A, 120B, 120C that controls a rate of delivery of the hemostatic agent during a procedure while minimizing instances of clogging, a user may reduce overall procedure time, increase efficiency and efficacy of procedures, and avoid unnecessary harm to a subject's body caused by clogging the medical device 100, 200 and/or ineffectiveness in coagulating the bleed.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device comprising:
   an agent including a plurality of particles of varying size;
   a handle including an enclosure for storing the agent; and
   a receiver having:
      a primary lumen with a cross-sectional dimension,
      a proximal end having a first cross-sectional dimension that is smaller than the cross-sectional dimension of the primary lumen, and
      a distal end having a second cross-sectional dimension that is smaller than the cross-sectional dimension of the primary lumen and the first cross-sectional dimension of the proximal end, such that the cross-sectional dimension of the primary lumen that is disposed between the proximal end and the distal end is greater than each of the first cross-sectional dimension and the second cross-sectional dimension;
   wherein the receiver has an axis extending between the proximal end and the distal end, the proximal end configured to receive all of the plurality of particles of varying size of the agent conveyed from the handle to the receiver, the distal end in fluid communication with an insertion portion including a lumen having a cross-sectional dimension smaller than the cross-sectional dimension of the primary lumen;
   wherein each of the cross-sectional dimension of the primary lumen, the cross-sectional dimension of the lumen of the insertion portion, the first cross-sectional dimension of the proximal end, and the second cross-sectional dimension of the distal end, is measured transverse to the axis;
   wherein the distal end is configured to receive the plurality of particles of varying size that are received inside the primary lumen from the proximal end of the receiver and allow only a first portion of the agent to exit the primary lumen and enter the lumen of the insertion portion based on a predefined particle size, such that a second portion of the agent including the particles having a size that exceeds the predefined particle size are inhibited by the distal end from exiting the primary lumen and entering the lumen of the insertion portion; and
   wherein the primary lumen is configured to collect the particles having the size that exceeds the predefined particle size between the proximal end and the distal end such that the second portion of the agent remains suspended in the primary lumen, the lumen of the insertion portion is configured to deliver the first portion of the agent based on the sizes of the first portion of the particles received in the lumen of the insertion portion not exceeding the predefined particle size.

2. The medical device of claim 1, wherein the handle includes a filter mechanism disposed within the enclosure, the filter mechanism is configured to inhibit at least a third portion of the agent from being conveyed to the receiver based on the size of the particles.

3. The medical device of claim 1, wherein the proximal end includes a proximal lumen having the first cross-sectional dimension, measured transverse to the axis, smaller than the cross-sectional dimension of the primary lumen, and greater than the cross-sectional dimension of the lumen of the insertion portion.

4. The medical device of claim 1, wherein the handle includes a filter mechanism disposed within the enclosure, the filter mechanism is configured to inhibit at least a third portion of the agent from being conveyed to the receiver based on the size of the particles.

5. The medical device of claim 3, wherein the proximal lumen is defined by and extends through the proximal end, and the distal end includes a distal lumen having the second cross-sectional dimension such that the distal lumen is defined by and extends through the distal end.

6. The medical device of claim 5, wherein a length along the axis of the primary lumen is greater than a length along the axis of each of the distal lumen and the proximal lumen.

7. The medical device of claim 1, wherein the distal end of the receiver includes an interface adjacent the primary lumen that is configured to control delivery of the agent from the primary lumen to the lumen of the insertion portion based on the sizes of the particles.

8. The medical device of claim 7, wherein the interface of the distal end is a planar surface extending transverse to the primary lumen, and defining an opening disposed along the planar surface that is in fluid communication with the lumen of the insertion portion.

9. The medical device of claim 7, wherein the interface of the distal end is a tapered surface defining an opening that is in fluid communication with the lumen of the insertion portion.

10. The medical device of claim 1, wherein the receiver is removably coupled to an exterior of the handle with the proximal end of the receiver coupled to a distal portion of the handle.

11. The medical device of claim 1, wherein the receiver is configured to mix the agent in the primary lumen and separate the plurality of particles based on the sizes of the plurality of particles;
  wherein the distal end of the receiver is configured to receive a particle of the particles in the lumen of the insertion portion when the size of the particle is equal to or less than the predefined particle size, and inhibit receipt of the particle in the lumen of the insertion portion when the size is greater than the predefined particle size such that the particle is deflected out of the distal end and returned into the primary lumen; and
  wherein the receiver is configured to deposit the particle along a bottom surface of the primary lumen, forming a static layer such that the particle is retained inside the primary lumen.

12. The medical device of claim 1, further including a plunger at least partially disposed within the enclosure, wherein the plunger is configured to move relative to the enclosure to move the agent within the enclosure.

13. The medical device of claim 12, wherein the plunger is configured to deliver a pressurized medium into the enclosure to move the agent toward the distal end of the receiver.

14. The medical device of claim 12, wherein the handle is coupled to the plunger, wherein the handle is configured to control movement of the plunger relative to the enclosure to control delivery of the agent from the enclosure to the receiver.

15. A medical device comprising:
  an agent including a plurality of particles of varying size;
  a handle for storing the agent; and
  a receiver including:
    a longitudinal axis;
    a primary lumen extending parallel to the longitudinal axis and having a cross-sectional dimension;
    a proximal end having a proximal lumen extending parallel to the longitudinal axis and having a first cross-sectional dimension; and
    a distal end having a distal lumen extending parallel to the longitudinal axis and having a second cross-sectional dimension;
  wherein the primary lumen is disposed between the proximal lumen and the distal lumen, and the cross-sectional dimension is greater than the first cross-sectional dimension and the second cross-sectional dimension;
  wherein the proximal lumen is configured to receive all of the plurality of particles of varying size conveyed from the handle to the receiver, the primary lumen is configured to retain a first portion of the particles that have a first size that is greater than a predefined particle size, and the distal lumen is configured to deliver only a second portion of the particles that have a second size that is smaller than the predefined particle size; and
  wherein the receiver is configured to suspend the first portion of the particles inside the primary lumen between the proximal lumen and the distal lumen as the second portion of the particles move through the primary lumen and into the distal lumen for delivery out of the receiver.

16. The medical device of claim 15, wherein the distal lumen is configured to inhibit delivery of the first portion of the particles that have the first size; and
  wherein the receiver is configured to deposit the first portion of the particles along a bottom surface of the primary lumen to form a static layer of the agent inside the primary lumen.

17. The medical device of claim 15, further including a ratchet configured to control a dose of the agent delivered to the receiver in response to actuation of the handle.

18. The medical device of claim 15, wherein the first size of the first portion of the particles is greater than the second cross-sectional dimension of the distal lumen, and the second size of the second portion of the particles is less than the second cross-sectional dimension of the distal lumen.

19. The medical device of claim 15, wherein each of the cross-sectional dimension, the first cross-sectional dimension, and the second cross-sectional dimension is measured transverse to the longitudinal axis.

20. A medical device comprising:
  an agent including a plurality of particles of varying size;
  a handle for storing the agent; and
  a receiver including a primary lumen having a cross-sectional dimension, a proximal end including a proximal lumen having a first cross-sectional dimension, and a distal end including a distal lumen having a second cross-sectional dimension, with the cross-sectional dimension of the primary lumen being greater than the first cross sectional dimension of the proximal lumen and the second cross-sectional dimension of the distal lumen, wherein the primary lumen is disposed between the proximal lumen and the distal lumen;
  wherein the proximal lumen is configured to receive all of the plurality of particles of varying size of the agent that is conveyed from the handle to the receiver, the primary lumen is configured to guide all of the plurality of particles of varying size from the proximal lumen towards the distal lumen, and the distal lumen is configured to:
    release a portion of the plurality of particles received from the primary lumen based on the portion of the plurality of particles having a dimension that is smaller than the second cross-sectional dimension of the distal lumen;
    inhibit release of a remainder of the plurality of particles received from the primary lumen based on the remainder of the plurality of particles having the dimension that is greater than the second cross-sectional dimension of the distal lumen; and
    deflect the remainder of the plurality of particles back into the primary lumen such that the plurality of particles having the dimension that is greater than the second cross-sectional dimension of the distal lumen is collected inside the primary lumen.

* * * * *